US011882852B2

(12) United States Patent
Tolborg et al.

(10) Patent No.: US 11,882,852 B2
(45) Date of Patent: Jan. 30, 2024

(54) PROCESS OF PRODUCING ALPHA-HYDROXY COMPOUNDS AND USES THEREOF

(71) Applicant: HALDOR TOPSØE A/S, Kgs. Lyngby (DK)

(72) Inventors: Søren Tolborg, Farum (DK); Juan Salvador Martínez Espín, Copenhagen (DK); Esben Taarning, Frederiksberg (DK)

(73) Assignee: HALDOR TOPSØE A/S, Kgs. Lyngby (DK)

(*) Notice: Subject to any disclaimer, the term of this patent is extended or adjusted under 35 U.S.C. 154(b) by 855 days.

(21) Appl. No.: 16/965,519

(22) PCT Filed: Jan. 23, 2019

(86) PCT No.: PCT/EP2019/051632
§ 371 (c)(1),
(2) Date: Jul. 28, 2020

(87) PCT Pub. No.: WO2019/154624
PCT Pub. Date: Aug. 15, 2019

(65) Prior Publication Data
US 2021/0045414 A1 Feb. 18, 2021

(30) Foreign Application Priority Data
Feb. 9, 2018 (DK) .............. PA 2018 00064

(51) Int. Cl.
| | | |
|---|---|---|
| *C07C 51/00* | (2006.01) | |
| *C07C 51/44* | (2006.01) | |
| *C07C 227/08* | (2006.01) | |
| *C07C 51/16* | (2006.01) | |
| *C07C 67/39* | (2006.01) | |
| *C07C 319/20* | (2006.01) | |
| *A23K 20/142* | (2016.01) | |
| *B01J 29/70* | (2006.01) | |
| *C07C 53/126* | (2006.01) | |
| *C07C 57/30* | (2006.01) | |
| *C08G 63/06* | (2006.01) | |
| *C08K 5/101* | (2006.01) | |
| *C08K 5/3417* | (2006.01) | |
| *C08K 5/3445* | (2006.01) | |

(52) U.S. Cl.
CPC ......... *A23K 20/142* (2016.05); *B01J 29/7049* (2013.01); *B01J 29/7057* (2013.01); *C07C 51/00* (2013.01); *C07C 51/16* (2013.01); *C07C 51/44* (2013.01); *C07C 53/126* (2013.01); *C07C 57/30* (2013.01); *C07C 67/39* (2013.01); *C07C 227/08* (2013.01); *C07C 319/20* (2013.01); *C08G 63/06* (2013.01); *C08K 5/101* (2013.01); *C08K 5/3417* (2013.01); *C08K 5/3445* (2013.01)

(58) Field of Classification Search
None
See application file for complete search history.

(56) References Cited

U.S. PATENT DOCUMENTS

| | | |
|---|---|---|
| 4,049,816 A | 9/1977 | Harnden et al. |
| 4,777,289 A | 10/1988 | Ruest |
| 5,139,563 A | 8/1992 | Astles et al. |
| 6,117,455 A | 9/2000 | Takada et al. |
| 2004/0022912 A1 | 2/2004 | Majerski et al. |
| 2010/0121096 A1* | 5/2010 | Taarning ............... C07C 51/00 560/179 |
| 2013/0197258 A1 | 8/2013 | Lauriol-Garbey et al. |
| 2017/0015614 A1 | 1/2017 | Orazov et al. |
| 2017/0369434 A1 | 12/2017 | Mahoney et al. |
| 2018/0118673 A1* | 5/2018 | Sadaba Zubiri ........ A23L 33/17 |
| 2019/0016675 A1 | 1/2019 | Mahoney et al. |

FOREIGN PATENT DOCUMENTS

| | | |
|---|---|---|
| CN | 1833531 A | 9/2006 |
| CN | 101024682 A | 8/2007 |
| CN | 101564088 A | 10/2009 |
| CN | 101898955 A | 12/2010 |
| CN | 105018384 A | 11/2015 |
| EP | 0245231 A1 | 11/1987 |
| EP | 1010667 B1 | 10/2003 |
| EP | 2184270 A1 | 5/2010 |
| JP | S51-125383 A | 11/1976 |
| JP | H03-20262 A | 1/1991 |
| JP | H08-151321 A | 6/1996 |
| JP | 2016-520050 A | 7/2016 |
| TW | 201202185 A | 1/2012 |
| TW | 201702220 A | 1/2017 |
| TW | 201803846 A | 2/2018 |
| WO | 97/000621 A1 | 1/1997 |

(Continued)

OTHER PUBLICATIONS

"Lewis Acid" (IUPAC. Compendium of Chemical Terminology, 2nd ed. (the "Gold Book"). Compiled by A. D. McNaught and A. Wilkinson. Blackwell Scientific Publications, Oxford (1997). Online version (2019-) created by S. J. Chalk. ISBN 0-9678550-9-8. https://doi.org/10.1351/goldbook) (Year: 1997).*
Holm ("Sn-Beta catalysed conversion of hemicellulosic sugars" Green Chemistry, 2012 (14), p. 702). (Year: 2012).*
Solvhoj ("Methyl vinyl glycolate as a diverse platform molecule" Green Chemistry, 2016(18), p. 5448) (Year: 2016).*
Mehtio, T. et al., "Copolymerization of glycolic, d,l-lactic and d,l-2-hydroxybutyric acid mixtures present in kraft black liquors" European Polymer Journal., Jan. 27, 2012, vol. 48, No. 4, pp. 774-778.
Office Action—Examination Report dated Sep. 9, 2021 by the Intellectual Property Office of Singapore in corresponding Singapore Patent Application No. 11202006314U, (7 pages).
Office Action dated Feb. 9, 2022, by the Intellectual Property India, Government of India in corresponding Indian Patent Application No. 202017028663, and an English Translation of the Office Action. (7 pages).

(Continued)

*Primary Examiner* — Amy C Bonaparte
(74) *Attorney, Agent, or Firm* — Boone IP Law

(57) ABSTRACT
New process of producing alpha-hydroxy compounds from sustainable resources useful as platform chemicals, such as hydroxy analogues of amino acids or polymer precursors.

17 Claims, No Drawings

(56) References Cited

FOREIGN PATENT DOCUMENTS

| WO | 2014179526 A1 | 11/2014 |
|---|---|---|
| WO | 2015024875 A1 | 2/2015 |
| WO | 2015067654 A1 | 5/2015 |
| WO | 2015/138742 A1 | 9/2015 |
| WO | 2016174231 A1 | 11/2016 |
| WO | 2017118871 A1 | 7/2017 |

OTHER PUBLICATIONS

Boschcov, P. et al."Ionization Constants and Thermodynamic Parameters of Histidine and Derivatives" Bioorganic Chemistry, vol. 12, No. 1, 1983, 11 pages.

Office Action (Notice of Reasons for Refusal) dated Jan. 13, 2023, by the Japanese Patent Office in corresponding Japanese Patent Application No. 2020-542805, and an English Translation of the Office Action. (15 pages).

Office Action (First Office Action) dated Sep. 20, 2022, by the State Intellectual Property Administration in corresponding Chinese Patent Application No. 201980012250.8, with English translation. (25 pages).

Wagner, J. et al."Gas chromatographic separation and determination of amino acids. II. Gas chromatographic separation and determination of amino acids in the form of methyl esters of hydroxy acids" Fresenius' Zeitschrift fuer Analytische Chemie, (1963), vol. 194, 1 page.

Bhandari, D. M., et al. "Tryptophan Lyase (NosI): A Cornucopia of 5′-Deoxyadenosyl Radical Mediated Transformations" Journal of the American Che:\Ical Society, vol. 138, 2016, pp. 16184-16187.

Office Action (Communication pursuant to Article 94(3) EPC) dated Jul. 22, 2021, by the European Patent Office In corresponding European Application No. 19 703 019.0-1109, (6 pages).

Van Der Heijden, G. et al.: "Metal-free one pot alpha-carboxylation of primary alcohols." Organic & Biomolecular Chemistry, vol. 14, No. 41, Jul. 1, 2016 (Jul. 1, 2016), pp. 9716-9719.

Verardo, G. et al.: "Exploring the reaction of iodine with alpha-diazo esters." Journal of Physical Organic Chemistry, vol. 22, No. 1, Jul. 1, 2021 (Jul. 1, 2021), pp. 24-30.

Nguyen, ST. et al: "A concise, total synthesis and antibacterial evaluation of 2-hydroxy-1-(1 H-indol-3-yl)-4-methylpentan-3-one" Bioorganic & Medicinal Chemistry Letters, Elsevier, Amsterdam, NL, vol. 20, No. 19, Oct. 1, 2010 (Oct. 1, 2010), pp. 5739-5742, XP027273552.

Gao, S. et al. "Ru-MACHO-Catalyzed Highly Chemoselective Hydrogenation of α-Keto Esters to 1,2-Diols or α-Hydroxy Esters" Synlett, vol. 27, No. 11, Jul. 8, 2021, pp. 1748-1752.

Poterala, M. et al.: "Synthesis of new chiral ionic liquids from alphahydroxycarboxylic acids.", Tetrahedron: Asymmetry, vol. 22, No. 3 , pp. 294-299, 2011.

Baldridge, R.: "The Metabolism of histidine. III. Urinary metabolites." Journal of Biological Science, vol. 233, Jul. 6, 2021, pp. 125-127.

Humphrey, A. J. et al. "Synthesis of Enantiomerically Pure alfa-Hydroxyaldehydes from the Corresponding alfa-Hydroxycarboxylic Acids: Novel Substrates for *Escherichia coli* Transketolase", J. Chem. Soc., Chem. Commun., 1995, vol. 24, pp. 2475-2476.

Bur, D. et al. "An evaluation of the substrate specificity and asymmetric synthesis potential of the cloned L-lactate dehydrogenase from Bacillus stearothermophilus1", Canadian Journal Chem., 1989, vol. 67, pp. 1065-1070.

Gudla, V. et al. "AuCl3/AgSbF6-catalyzed rapid epoxide to carbonyl rearrangement", Tetrahedron Letters, 2012, vol. 53, No. 39, pp. 5243-5247.

Uchida, R. et al. "Kurasoins A and B, New Protein Earnesyltransferase Inhibitors Produced by *Paecilomyces* sp. FO-3684, II Structure Elucidation and Total Synthesis", The Journal of Antibiotics, Sep. 1996, vol. 49, No. 9, pp. 886-889.

Jahn, U. "Highly Efficient Generation of Radicals from Ester Enolates by the Ferrocenium Ion. Application to Selective α-Oxygenation and Dimerization Reactions of Esters", J. Org. Chem. 1998, 63, pp. 7130-7131.

Fritz-Langhals, E. et al. "Simple synthesis of optically active 2-fluoropropanoic acid and analogs of high enantiomeric purity", Tetrahedron Letters, 1993, vol. 34. No. 2, pp. 293-296.

Noordam, A. et al. "Stereoselective synthesis of (+)-pilocarpine, an imidazole alkaloid used in ophthalmology", Recl. Trav. Chim. Pays-Bas, 1979, vol. 98, No. 7-8, pp. 467-468.

Papulov, Y.G. "The Relationship of the properties of substances with the structure of molecules: Mathematical modeling" Advances of Modern Natural Science, 2006, No. 2, pp. 75-76. (With English Translation).

Mihaijlin, IO, A. "Special polymeric composite materials", Publishing house HOT, Science and Technology, St. Petersburg, 2009,2 page. (With English Translation).

Office Action dated May 31, 2022, by the Taiwan Intellectual Property Office in corresponding Taiwanese Patent Application No. 108103790, and an English Translation of the Office Action. (12 pages).

Danish Search Report dated Jun. 8, 2018, issued in corresponding Danish Patent Application No. PA 2018 00064. (8 pages).

International Search Report (PCT/ISA/210) dated May 16, 2019, by the European Patent Office as the International Searching Authority for International Application No. PCT/EP2019/051632.

Written Opinion (PCT/ISA/237) dated May 16, 2019, by the European Patent Office as the International Searching Authority for International Application No. PCT/EP2019/051632.

\* cited by examiner

PROCESS OF PRODUCING ALPHA-HYDROXY COMPOUNDS AND USES THEREOF

TECHNICAL FIELD

The present invention regards a new process for producing alpha-hydroxy compounds useful as platform chemicals, such as hydroxy analogues of amino acids or polymer precursors.

BACKGROUND

In animal nutrition there is a great demand for feed additives. A group of feed additives are amino acids and hydroxy analogues of amino acids. In particular, there is a demand for biobased feed additives made from, renewable, sustainable raw materials. The amino acids Leucine (Leu), Isoleucine (Ile), Valine (Val), Phenylalanine (Phe) Histidine (His), Methionine (Met), Cysteine (Cys), Glutamic acid (Glu), Tryptophan (Trp) and Tyrosine (Tyr) are all interesting as additives in animal feed. But also the corresponding amino acid analogues may be used. In order to be useful as feed additives, low cost processes for producing the amino acids or the alpha-hydroxy analogues are needed. Known processes include fermentation and various processes of chemical synthesis.

Both Lysine and Methionine can be mentioned as exemplary amino acids which are successfully used as additives in animal nutrition. Both in its natural forms and as the hydroxy analogues, They have been produced both by fermentation and by chemical synthesis.

WO 2017/118871 discloses a process for the fermentative production of L-methionine and its derivatives from sugars.

WO 2016/174231 discloses a process for producing methionine alpha-hydroxy analogue and derivatives thereof by contacting one or more sugars with a metallo-silicate composition in the presence of a compound comprising sulphur and a solvent. Yields of more than 30% were obtained.

The most successful and economical ways of producing amino acids for industrial use so far, seems to be by fermentation of biobased raw materials using genetically modified microorganisms. So far no chemical process has been found to be effective in producing amino acids other than methionine.

There is thus still a need for environmentally friendly, economic processes for producing biobased amino acids and hydroxy analogues thereof from renewable, sustainable raw materials which processes are economical, flexible and suitable for large scale, industrial production.

SUMMARY OF INVENTION

It has surprisingly been found by the present inventors that a number of important amino acids may be obtained in their hydroxy analogue form by chemo-catalytically combining glycolaldehyde (GA, first compound) and certain chemical compounds (second compound) by a simple, sustainable process, which is flexible and suitable for industrial scale production.

A first aspect disclosed herein relates to a process for producing an alpha-hydroxy reaction product of the formula I:

(R)CH(R')—CHOH—COOR"  (I)

Wherein
R is —H or —CH$_3$;
R' is —CH$_3$, —CH$_2$CH$_3$, —CH(CH$_3$)$_2$, —C$_6$H$_5$, —CH$_2$SCH$_3$, —C$_8$H$_6$N or —C$_3$H$_3$N$_2$; and
the process comprising the steps of
a) Providing a first compound of the formula II:

HO—CH2—CH=O  (II)

b) Providing a second compound of the formula III:

R—CO—R'  (III)

Wherein
R and R' have the meanings as defined above; and
c) Reacting the first compound with the second compound in the presence of a Lewis acid catalyst to provide an alpha-hydroxy reaction product.

Advantages of this process is that it is suitable for up-scaling and it is thus suitable for large scale production of alpha-hydroxy amino acid analogs by a process which is flexible and efficient and allows for the use of biobased starting materials, obtainable from renewable, sustainable raw materials.

Step c) may take place in a reaction zone, such as in a reactor fluid (i.e. reaction mixture). After having reacted first and second compounds (reactants), the reaction mixture will contain any unreacted reactants and any alpha-hydroxy reaction products formed. The reaction is envisaged to take place in a reactor containing the Lewis acid catalyst. The system for producing an alpha-hydroxy reaction product according to the present invention is quite flexible, since the same catalyst may be used to produce a variety of alpha-hydroxy reaction products, optionally in a one-pot process using two or more different compounds of formula (III). In addition the first compound is the same irrespective of which alpha-hydroxy reaction product it is desired to produce.

A second aspect disclosed herein relates to a compound of the formula I:

(R)CH(R')—CHOH—COOR"  (I)

Wherein
R is —H or —CH$_3$;
R' is —CH$_3$, —CH$_2$CH$_3$, —CH(CH$_3$)$_2$, —C$_6$H$_5$, —CH$_2$SCH$_3$, —C$_8$H$_6$N or —C$_3$H$_3$N$_2$; and
R" is —H, —CH$_2$CH$_3$, —CH(CH$_3$)$_2$, —CH$_2$CH$_2$CH$_3$, —CH$_2$CH$_2$CH$_2$CH$_3$, —CH$_2$CH(CH$_3$)$_2$, or —C(CH$_3$)$_3$ A third aspect disclosed herein relates to an animal feed composition comprising one or more compounds of the formula I and an animal feed component.

A fourth aspect disclosed herein relates to a use of one or more compounds of the formula I for preparing an animal feed composition.

A fifth aspect disclosed herein relates to a use of one or more compounds of the formula I for preparing a polymer.

DETAILED DISCLOSURE OF THE INVENTION

Definitions

Where nothing eke is stated, "active metal" is meant to refer to the metal atom in a catalytically active form.

Compound 1 is meant to refer to Glycolaldehyde and may also be referred to as first compound. It may appear in monomeric, dimeric or oligomeric form. Compound 2 is meant to refer to an aldehyde or ketone compound of the formula (III) and may also be referred to as second compound. It may appear in monomeric, dimeric or oligomeric form. Compounds 1 and 2 may alternatively be referred to as reactants or substrates. The alpha-hydroxy reaction product may be referred to simply as "reaction product". If more than one compound of formula (III) is added to the same reaction mixture or reaction zone, also more than one alpha-hydroxy reaction products (formula (I)) will be obtained. It may be referred to in singularis even if several reaction products are formed.

Where nothing else is stated, concentrations given in percentages are to be understood as weight% (i.e. weight of x per total weight of solution times 100%). Where nothing else is stated, when referring to concentrations of compounds which may dimerize in solution, the concentrations given refer to the concentration of the monomer equivalents, e.g. for first and second compound as well as for the alpha-hydroxy reaction product.

The term "Recovering" is meant to refer either to collecting the alpha-hydroxy reaction product or to directing the reaction mixture comprising the alpha-hydroxy reaction product to a subsequent step, such as to a purification unit.

The term "yield" is in the present context meant to refer to the molar percentage of carbon of the first compound (glycolaldehyde) which is recovered in the desired alpha-hydroxy reaction product formed. Accordingly, if 100 mmol of the glycolaldehyde reactant (first compound) was converted into 50 mmol alpha-hydroxy reaction product, then half of the carbon atoms of the initial glycolaldehyde would be recovered in the alpha-hydroxy reaction product, and thus the yield would be 50%; in the case of formation of MVG, 100 mmol glycolaldehyde converted into 50 mmol of MVG would correspond to a yield of 100%, since two molecules of glycolaldehyde are needed to form one molecule MVG.

The term "conversion" is in the present context meant to refer to the molar fraction of glycolaldehyde (first compound) which has reacted during step c) to form either the desired alpha-hydroxy reaction product or other compounds.

The term "selectivity" is meant to refer to the molar fraction of desired alpha-hydroxy reaction product formed per glycolaldehyde converted.

In the present context, a "reaction zone" is meant to refer to the area around the catalyst wherein the first and second compounds are brought into contact with the Lewis acid catalyst and the two compounds react. In certain embodiments the reaction zone may be defined by the walls of the chemical reactor. In a continuous reactor, the reaction zone may be defined by the reactor walls and the inlet and the outlet. The reaction zone may alternatively be defined by the interface between the reaction mixture contained within the reactor and the surroundings.

The "reaction mixture" is meant to refer to the mixture present in the reaction zone, including e.g. any unreacted first and second compounds (reactants) and the alpha-hydroxy acid compound (alpha-hydroxy reaction product) formed and any by-products or solvents or diluents present. In an embodiment, step c) takes place in such a reaction mixture, The reaction mixture may also be termed "reactor fluid". When recovering a product stream from the reaction zone all of the compounds present in the reaction mixture will be present to some extent.

The term "continuous process" is meant to refer to a process carried out under continuous conditions or steady state conditions. Accordingly there will not be major concentration fluctuations. In a continuous process first and/or second compounds (the reactants) are continuously fed to a reaction zone and the reaction product is continuously recovered from the reaction zone. In this context "continuously feeding" and "continuously recovering" includes repeatedly feeding small portions of the reactants to the reaction zone and repeatedly recovering small portions of the alpha-hydroxy acid product composition from the reaction zone. Also, the reactants may be fed to the reaction zone in several positions and the product may be recovered from several positions (such as in a fluid bed reactor or packed bed reactor, optionally with recycle of excess second compound to the feed stream or to the reactor inlet)

Where nothing else is stated, the radicals R, R' and R" have the following meanings:

R is —H or —CH$_3$;

R' is —CH$_3$, —CH$_2$CH$_3$, —CH(CH$_3$)$_2$, —C$_6$H$_5$, —CH$_2$SCH$_3$, —C$_8$H$_6$N or —C$_3$H$_3$N$_2$; and R" is —H, —CH$_2$CH$_3$, —CH(CH$_3$)$_2$, —CH$_2$CH$_2$CH$_3$, —CH$_2$CH$_2$CH$_2$CH$_3$, —CH$_2$CH(CH$_3$)$_2$, or —C(CH$_3$)$_3$ There is a demand for animal feed additives which are biobased and obtainable by economical processes suitable for large scale production. Such a process is provided by the process according to the present invention. The inventors found that Lewis acid catalysts have excellent catalytic activity in facilitating the reaction between glycolaldehyde (first compound) and one or more specific aldehydes or ketones (second compound) according to the reaction scheme:

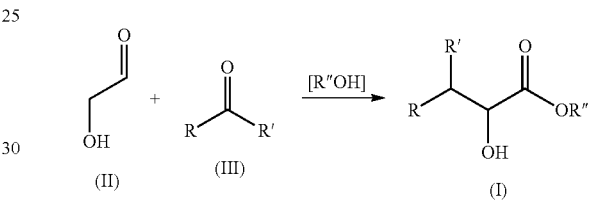

The resulting one or more alpha-hydroxy reaction products are alpha-hydroxy compounds. An alpha-hydroxy compound has a structure which resembles the backbone of amino acids, except for the alpha-hydroxy group, which must be replaced with an amino group to be converted into the corresponding amino acid. Accordingly, the radicals R and R' may be selected to correspond to amino acid side groups. Depending on the environment in the reaction zone, the alpha-hydroxy reaction product may be in acid form (in which case R" is H) or it may be in ester form (in which case. R" is an alkyl group).

The inventors surprisingly found, that Lewis acid catalysts catalyzed the condensation reaction between glycolaldehyde and ketones or aldehydes of the structures given herein. Not only did the. Lewis acid catalysts catalyze the above reaction, they also favoured the isomers relevant for preparing alpha-hydroxy amino acid analogs and the yields were quite high. The inventors surprisingly found that for the methionine-hydroxy analogue, a benefit of the process according to the present invention is that the methyl mercapto group will be positioned exclusively on the carbon number 4 from the carboxyl group, when starting out from compounds corresponding to first and second compounds in the presence of a Lewis acid catalyst.

When contacting the first compound with the second compound in the presence of a Lewis acid catalyst, the two compounds react and surprisingly, an alpha-hydroxy reaction product is favoured. Without being bound by theory it is hypothesized that the first compound (which is glycolaldehyde) acts as the more reactive species, favoring primarily the formation of the alpha-hydroxy ester. The reaction scheme below illustrates the hypothesized reaction mechanism of glycolaldehyde reacting with the second compound.

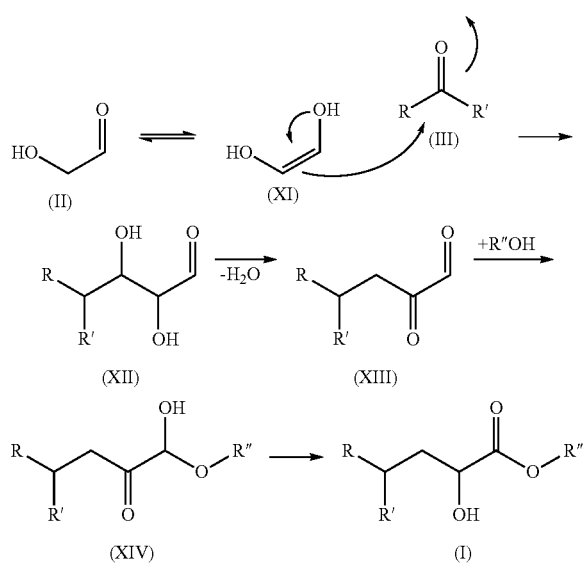

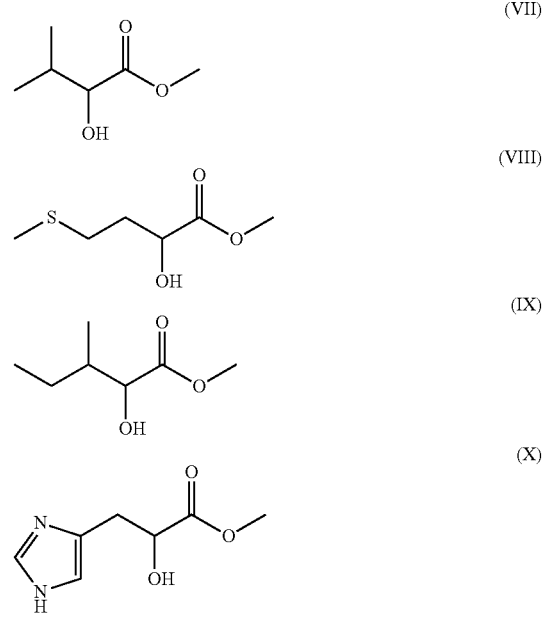

The alpha-hydroxy reaction product is a carboxylic acid or an ester with a hydroxy group in the C2 carbon position, relative to the carboxylic acid/ester group. The nature of radical R" will depend on the environment of the first and second compounds in step c). In an aqueous solution the acid form is favoured (R" is —H). In a solvent comprising an alcohol, the corresponding ester will be favoured. Accordingly, methanol will favour formation of the methyl ester (R" is —CH$_3$), ethanol will favour the ethyl ester (R" is —C$_2$H$_5$) etc. According to an embodiment of the present invention, the alpha-hydroxy reaction product of the formula I is an alpha-hydroxy amino acid analog. In an embodiment according to the present invention, the alpha-hydroxy reaction product is selected from the group consisting of: methyl 2-hydroxy-3-phenylpropanoate (IV), methyl 2-hydroxy-4-methylpentanoate (V), methyl 2-hydroxy-3-(1H-indol3-yl)-propanoate (VI), methyl 2-hydroxy-3-methylbutanoate (VII), methyl 2-hydroxy-4-methylsulfanylbutanoate (VIII), methyl 2-hydroxy-3-methylpentanoate (IX) and methyl 2-hydroxy-3-(1H-imidazol-4-yl)-propanoate (X). The compounds may be represented by the structures:

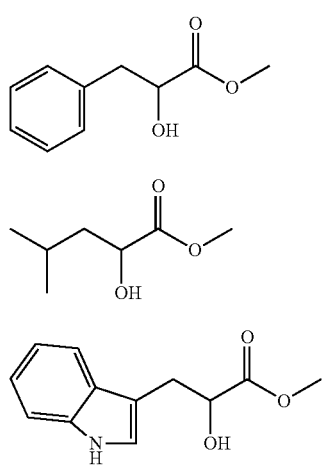

In the process according to the present invention the first compound is glycolaldehyde. In an embodiment according to the present invention, the concentration of the first compound in the reaction mixture is in the range of from of 0.1 to 30 wt %, such as from 0.1 to 20 wt or 1 to 5 wt %.

In the process according to the present invention the second compound is a ketone or an aldehyde carrying a substituent (R') which corresponds to the side chain of an amino acid. If R is CH$_3$ the second compound is a ketone. If R is H, the second compound is an aldehyde. The second compound may be provided in a solvent. In an embodiment a mixture of solvents may be used. In this case more than one alpha-hydroxy reaction product may be co-produced. In an embodiment according to the present invention, the concentration of second compounds in the reaction mixture is in the range of from 0.9 and 60 wt %, such as from 0.9 to 40 or from 7 to 15 wt %. In an embodiment according to the present invention, the combined concentration of first and second compounds in the reaction mixture is in the range of from 1 and 50 wt %, such as from 5 to 20 or from 8 to 15 wt %.

First and second compounds may be present in various forms such as monomer, dimer, acetal or oligomer, depending on its physical state and of the chemical environment (such as solvent). All forms of the first and second compounds are encompassed in the present invention. In an embodiment according to the present invention, the glycolaldehyde is provided as a glycolaldehyde dimes, glycolaldehyde diethyl acetal or as glycolaldehyde dimethyl acetal. When the first and second compound are provided in solution, it may e.g be provided in the form of an acetal in the solution and then in the reaction zone it is hydrolyzed to yield the aldehyde or ketone corresponding to first and/or second compound. Accordingly, the first and/or second compound may e.g. be provided in solvents or they may be bubbled through a reactor fluid.

Also the alpha-hydroxy reaction product may be present in various forms, such as monomer, dimer, acetal or oligomer, depending on its physical state and of the chemical environment (such as solvent). All the above-mentioned forms of the alpha-hydroxy reaction product are encompassed in the present invention. The alpha-hydroxy reaction product may be recovered in a solvent.

According to an embodiment of the present invention, two or more second compounds are provided and in step c) two or more alpha-hydroxy reaction products are accordingly obtained. According to an embodiment of the present invention, the total yield of the one or more alpha-hydroxy reaction product of the formula I is in the range of from 10-99%, such as from 15-99%.

In an embodiment according to the present invention, the second compound is provided in stoichiometric excess of the first compound. An advantage of having the second compound in excess is that self-condensation of glycolaldehyde during reaction is reduced. Accordingly, the molar ratio between the first and second compound is preferably in the range of from 0.01 to 1, such as from 0.01 to 0.8 or 0.01 to 0.5.

In an embodiment according to the present invention, the second compound is a ketone (compound of formula I has R =$CH_3$). In a preferred embodiment, the molar ratio between the ketone and the first compound is in the range of from 1 to 50, such as from 5 to 30 or 8 to 30.

In an embodiment according to the present invention, the second compound is an aldehyde (compound of formula I has R =In a preferred embodiment, the molar ratio between the aldehyde and the first compound is in the range of from 1 to 50, such as from 5 to 30 or 8 to 30.

The Lewis acid catalyst (or Lewis acid material) act as an electron pair acceptor to increase the reactivity of a substrate. It may be a metallosilicate material in which case it is a heterogenous catalyst. However, homogenous Lewis acid catalysts, such as metal salts, may also be suitable in the present invention.

A metallosilicate material (also known as metallosilicates, metallosilicate composition or metallosilicate catalyst) refers to one or more solid materials comprising silicon oxide and an active metal (optionally in the form of a metal oxide component), wherein the active metal and/or metal oxide components are incorporated into (such as grafted onto) the surface of the silicon oxide structure (i.e. the silicon oxide structure comprises M—O—Si bonds). The silicon oxide structure is also known as a silicate and the silicon oxide structure incorporating the active metal is correspondingly known as a metallo-silicate. Metallo-silicate materials may be crystalline or non-crystalline. Non-crystalline metallosilicate materials include ordered mesoporous amorphous forms and other mesoporous amorphous forms. Crystalline microporous material includes zeolite materials and zeotype materials. According to an embodiment of the present invention, the Lewis acid catalyst has a zeolite framework structure, which is selected from the group consisting of BEA, MFI, FALL, MOR, FER and MWW. In another embodiment, the Lewis acid catalyst has the mesoporous structure MCM-41 and SBA-15.

Zeolite materials are crystalline aluminosilicates with a microporous crystalline structure, according to Corma et al., Chem. Rev. 1995, 95 pp 559-614. The aluminum atoms of the zeolite material may be partly or fully substituted by an active metal (see e.g. WO/2015/067654); these materials fall within the class of zeotype materials. For the purpose of the present invention zeotype materials encompass zeolite materials and the metallosilicate is substituted with an active metal imparting Lewis acidity to the material. Lewis Acid catalysts act as an electron pair acceptor to increase the reactivity of a substrate. In the present context, the Lewis Acid catalysts catalyze the aldol condensation reaction between compound 1 (glycolaldehyde) and the selected compound 2 to obtain the targeted amino acid alpha-hydroxy analogue. According to an embodiment of the present invention, the Lewis acid catalyst comprises an active metal selected from one or more of the groups consisting of Al, Sn, Ti, Pb, Zr, Zn, V, Nb, Ta, Ge and Hf, preferably from Sn, Zr, Ge and Hf, most preferred it is Sn.

According to an embodiment of the present invention, the Lewis Acid catalyst is selected from the group consisting of Sn-BEA, Sn-MCM-41 and a soluble tin salt. The soluble tin salt may be selected from the group consisting of tin chloride ($SnCl_4$ and $SnCl_2$), tin fluoride ($SnF_4$ and $SnF_2$), tin bromide ($SnBr_4$ and $SnBr_2$), tin iodide ($SnI_4$ and $SnI_2$), tin acetylacetonate ($SnClOH14O4$), tin pyrophosphate ($Sn_2P_2O_7$), tin acetate ($Sn(CH3CO2)_4$ and $Sn(CH3CO2)_2$), tin oxalate ($Sn(C2O4)_2$ and $SnC2O4$), tintriflate ($Sn(CF3SO3)_2$ and $Sn(CF3SO3)_4$), Corresponding salts of e.g. Al, Ti, Pb, Zr, Zn, V, Nb, Ta, Ge and Hf will also be suitable for use as Lewis acid catalysts in the present invention.

According to an embodiment of the present invention no other aldehydes or ketones are present in step c) than the first and second compounds.

According to an embodiment of the present invention, step c) is carried out at a temperature in the range of from 30 to 220° C., such as from 60 to 180 C. In an embodiment of the present invention, in step c), the first and second compounds are reacted for a period of time in the range of from 10 seconds to 48 hours. The time needed will depend on various factors such as first and second compound ratio and concentrations as well as amount of catalyst added relative to the two reactants as well as the temperature chosen.

The process described herein may be carried out in a reactor comprising a reaction vessel, one or more reactant inlets and one or more product outlets. The process may be carried out as a batch process or or as a continuous process.

According to an embodiment of the present invention, the process disclosed herein is operated as a batch process. In an embodiment disclosed herein a system is provided for performing the batch process as described herein, said system comprising a batch reactor or a fed batch reactor.

According to an embodiment of the present invention, the process disclosed herein is operated as a continuous process and the starting material is fed to the reaction zone at a rate of 0.01-400 g(glycolaldehyde)/(g(catalyst)/hr) (Weight Hourly Space Velocity, WHSV). In an embodiment disclosed herein a system is provided for continuously performing the process according to the present invention, said system comprising a fixed bed reactor (plugged flow reactor, PER) or a continuously stirred tank reactor (CSTR).

In an embodiment, step c) is conducted in the presence of a solvent. Suitably, the first and/or second compound is provided in the form of a feedstock comprising compound 1 or compound 2 and a solvent. In an embodiment according to the present invention, the solvent is a polar or slightly polar solvent, In an embodiment according to the present invention, the solvent has a dielectric constant above 15. Exemplary solvents are DMSO, dimethylformamide, acetic acid, acetonitrile, methanol, ethanol, propanol, isopropanol, n-butanol, tert-butanol, acetone, benzaldehyde, butanone, isobutyraldehyde, 1H-imidazole-4-carbaldehyde, 1H-indole-3-carbaldehyde and methylsulfanyl-acetaldehyde, water or mixtures thereof. In an embodiment, the solvent is selected from the group consisting of water, methanol, and ethanol; or mixtures thereof. In an embodiment the second compound and the solvent is the same. In this case, the second compound is provided in excess of at least 1:2, such as 1:5 or 1:10 (first compound:second compound). An advantage of using polar or slightly polar solvents is that the solubility of first compound is high, which results in yields of the alpha-hydroxy reaction product in excess of 10%. Preferably, the yield of the alpha-hydroxy amino acid analogue is higher than 10%, 20%, 30%, 40%, 50%, 60% or even as high as 70%. In an embodiment according to the present invention the yield of the alpha-hydroxy reaction product is in the range of from 10-99%, such as from 10-70% or from 30-60%.

In an embodiment according to the present invention the molar ratio of silicon to active metal is between 10 and 1000, such as between 20 and 400, between 50 and 200, or between 75 and 125.

According to a further embodiment of the invention, the Sn-BEA is prepared by a direct synthesis process using hydrogen fluoride or by a post treatment process. Examples of direct synthesis processes are described in EP 1 010 667 B1. An example of a post treatment process for the preparation of Sn-BEA is illustrated in WO2015/024875 A1.

In an embodiment, as disclosed herein, the first compound is obtained from a renewable, sustainable, biobased raw material. Glycolaldehyde may e.g. be obtained from ethylene glycol or sugar. In an embodiment, the first compound as disclosed herein is derived from pyrolysing a sugar such as glucose or sucrose, such as described in US 2004/0022912. The glycolaldehyde may in an embodiment be provided as an aqueous solution comprising glycolaldehyde in an amount of 1-99 wt/wt % and pyruvaldehyde in an amount of 0.1-60 wt/wt %, such as in an amount of 0.1-40 wt/wt %, such as in an amount of 0.1-30 wt/wt %. In a further embodiment, the aqueous solution further comprises acetol in an amount of 0.1-40 wt/wt %, such as in an amount of 0.1-20 wt/wt %, such as in an amount of 0.1-10 wt/wt %. In a further embodiment the aqueous solution further comprises glyoxal in an amount of 0.1-40 wt/wt %, such as in an amount of 0.1-20 wt/wt %, such as in an amount of 0.1-10 wt/wt %. In a further embodiment, the aqueous solution further comprises formaldehyde in an amount of 0.1-60 wt/wt %, such as in an amount of 0.1-40 wt/wt %, such as in an amount of 0.1-20 wt/wt %.

In an embodiment according to the present invention, the process comprises a further step d) of recovering the one or more alpha hydroxy reaction product. Suitably, the one or more alpha hydroxy reaction products are recovered by distillation or extraction.

In an embodiment, the process according to the present invention, comprises a further step e) of aminating the alpha hydroxy reaction product to yield the corresponding amino acid compound. This may suitably be carried out in an enzymatic process. Suitably, steps c) and e) described above may be carried out in the same reactor, in a "one-pot" combined process. The reactor could be a batch reactor, a fed batch reactor or a chemostat.

The alpha-hydroxy reaction products according to the present invention as well as the corresponding aminated alpha-hydroxy reaction products according to the invention are suitable as animal feed additives. Similarly, the alpha-hydroxy reaction products according to the present invention as well as the corresponding aminated alpha-hydroxy reaction products are suitable as human food additives. For both uses they may be mixed with one or more animal feed or human food components, such as a carrier material, a carbohydrate, an adjuvant, an anti-caking agent, an antioxidant, or a surfactant, to form an animal feed or human food composition. The additives or compositions may be formulated into a solution, suspension, pellets, powder etc. as is known in the art.

The alpha-hydroxy reaction products according to the present invention are also envisaged to be suitable as monomers for preparing polymers. They may may also be combined with other monomers, such as lactic acid, lactide, ethylene glycol or glycolic acid, to prepare a co-polymer.

EXAMPLES

In the following examples the preparation of catalysts and production of alpha-hydroxy analogues of amino acids from glycolaldehyde are illustrated.

Example 1

Preparation of Metallosilicate Materials Via Post-Synthesis Procedure

Example 1A

Process for the Preparation of Sn-BEA Via Post-Treatment Process

Post-synthesized Sn-BEA zeolite/zeotype materials were prepared according to the procedure described in ChemSusChem 2015, 8, 613-617. A commercial BEA zeolite having the *BEA framework (CP7119, Zeolyst, Si/Al=12.5, $NH_4^+$-form) was initially calcined at 550° C. for 6 h to obtain the zeolite on its H+-form, followed by acidic dealumination as follows: 10 g of concentrated nitric acid (HNO3, Sigma-Aldrich, ≥65%) was added per 1 g of zeolite *BEA material and the suspension was heated to 80° C. for 12-24 h. The dealuminated solid was recovered by filtration, extensively washed with deionized water and calcined at 550° C. for 6 h using a heating ramp of 2° C./min. Tin was then introduced in the created vacancies in the zeolite framework by incipient wetness impregnation using tin(II) chloride in solution as the tin source. The solution was prepared by dissolving 0.128 g of tin(II) chloride (Sigma-Aldrich, 98%) in 5.75 mL of water and the solution was added to 5 g of the dealuminated *BEA zeolite sample. Following impregnation, the sample was dried overnight at 110° C. and then calcined at 550° C. for 6 h.

Example 1B

Preparation of Zr-BEA Via Post-Treatment Process

The same procedure as for 1A was followed, except the 0.128 g of tin(II) chloride was replaced with 0.121 g $ZrOCl_2 \cdot 8H_2O$ or $ZrCl_4$ was used as the source of zirconium.

Example 1C

Preparation of Ti-BEA Via Post-Treatment Process

The same procedure as for 1A was followed, except the 0.128 g of tin(I) chloride was replaced with 0.154 g titanium (IV) ethoxide ($Ti(OC_2H_5)_4$, Sigma-Aldrich) as the source of titanium. The titanium source was furthermore dissolved in a 50:50 mixture of water and hydrogen peroxide instead of pure water during impregnation.

Example 1D

Preparation of Zn-BEA Via Post-Treatment Process

The same procedure as for 1A was followed, except the 0.128 g of Sn(ll) chloride was replaced with 0.091 g Zn(II) chloride as the source of zink.

Example 1E

Preparation of Hf-BEA Via Post-Treatment Process

The same procedure as for 1A was followed, except the 0.128 g of Sn(II) chloride was replaced with 0.216 g Hf(IV) chloride as the source of hafnium.

Example 1F

Preparation of Ge-BEA Via Post-Treatment Process

The same procedure as for 1A was followed, except the 0.128 g of Sn(ll) chloride was replaced with 0.070 g Ge(IV) oxide as the source of germanium.

Example 2

Preparation of Metallosilicate Materials Via Direct Synthesis Procedure

Example 2A

Preparation of Sn-BEA Via a Direct Synthesis Method

Sn-BEA zeolites prepared by direct hydrothermal synthesis were synthesized by the route described in J. Mater. Chem A 2014, 2, 20252-20262.1n this preparation, 30.6 g of tetraethyl orthosilicate (TEOS, 98%, Aldrich) was added to 33.1 g of tetraethylammonium hydroxide (TEAOH, 35% solution, Aldrich) under stirring. After a single phase was obtained, 0.336 g of tin(IV) chloride pentahydrate (SnCl4·H2O, Sigma-Aldrich) was dissolved in 2.0 mL of $H_2O$ and added slowly. Following several hours of stirring (>5 h), a thick gel was formed and then finalized by the addition of 3.1 g HF in 1.6 g of demineralized $H_2O$. The sample was homogenized and transferred to a Teflon-lined container and placed in a stainless steel autoclave and heated statically at 140° C. for 14 days. The solid was recovered by filtration, washed thoroughly with demineralized water and dried overnight at 80 ° C. in air. To remove the organic template and finalize the material, it was calcined at 550° C. for 6 h using a heating ramp of 2° C/min.

Example 2B

Preparation of Zr-BEA Via a Direct Synthesis Method

The sme procedure as for 2A was followed, except the 0.336 g of tin(IV) chloride pentahydrate was replaced with 0.318 g $ZrOCl_2·8H_2O$ or $ZrCl_4$ as the source of zirconium.

Example 2C

Preparation of Ti-BEA Via a Direct Synthesis Method

The same procedure as for 2A1D was followed, except the 0.336 g of tin(IV) chloride pentahydrate was replaced with 0.405 g titanium(IV) ethoxide ($Ti(OC_2H_5)_4$, Sigma-Aldrich) as the source of titanium. The titanium source was furthermore dissolved in a 50:50 mixture of water and hydrogen peroxide instead of pure water during impregnation.

Example 2D

Preparation of Sn-MFI Via a Direct Synthesis Method

MFI zeolites/zeotypes were prepared following the procedure described in Microporous Mater. 1997, 12, 331-340. To prepare Sn-MFI (Si/Sn=100), 0.257 g of tin(IV) chloride pentahydrate (SnCl4·5H2O, Aldrich, 98%) was dissolved in 5 g of demineralized water and added to 15.6 g of tetraethyl orthosilicate (TEOS, 98%, Aldrich) and stirred for 30 min. To this solution, 13.4 g of tetrapropylammonium hydroxide (TPAOH, 40%, AppliChem) in 13.4 g of demineralized water was then added and stirred for 1 h. Following this, an additional 60 g of demineralized water was added and the solution was stirred for another 20 h, whereafter the solution was added to a Teflon-lined autoclave and synthesized at 160° C. for 2 days under static conditions. The solid was recovered by centrifugation, washed thoroughly with demineralized water and dried overnight at 80° C. in air. To remove the organic template and finalize the material, it was calcined at 550° C. for 6 h using a heating ramp of 2° C./min.

Example 2E

Process for the Preparation of TS-1 (Ti-MFI) Via Hydrothermal Process

The same procedure as for 2D was followed, except 0.257 g of tin(IV) chloride pentahydrate was replaced with 0.167 g titanium(IV) ethoxide (Ti(OC2H5)4, Sigma-Aldrich) as the source of titanium. The titanium source was furthermore dissolved in a 50:50 mixture of water and hydrogen peroxide instead of pure water during impregnation.

Example 2F

Preparation of Sn-MCM-41 Via Hydrothermal Process

The ordered mesoporous stannosilicate Sn-MCM-41 was prepared according to the route described in Green Chem. 2011, 13, 1175-1181. 26.4 g of tetraethylammonium silicate (TMAS, Aldrich, 15-20 wt % in water, ≥99.99%) was slowly added 13.0 g of hexadecyltrimethylammonium bromide (CTABr, Sigma, ≥99.0%) dissolved in 38.0 g of water. This mixture was then stirred for 1 h followed by addition of 0.239 g tin(IV) chloride pentahydrate (SnCl4·5H2O , 98%, Aldrich) and 0.537 g hydrochloric acid (HCl, Sigma-Aldrich, min. 37%) in 2,1 g of water. This solution was stirred for 1.5 h before 12.2 g of tetraethyl orthosilicate (TEOS, 98%, Aldrich) was added and stirred for an additional 3 h, The resulting mixture was transferred to a Teflon-lined container placed in a stainless steel autoclave and heated to 140° C. for 15 h. The solid was recovered by filtration, washed thoroughly with demineralized water and dried overnight at 80° C. in air. To remove the organic template and finalize the material, it was calcined at 550° C. for 6 h using a heating ramp of 2° C./min.

Example 3

Preparation of Valine Hydroxy Analogue from GA and Acetone

Example 3A. For the preparation of valine hydroxy analogue, 10 g of an acetone/GA solution composed of 0.1 g GA, 5 g acetone and 4.9 g anhydrous methanol was premixed and added to a stainless steel pressure vessel (40 cc, Swagelock) along with 0.50 g of post-synthesized Sn-BEA (Si/Sn=125). This batch reactor was then sealed and placed in a pre-heated oil bath at 160° C. under 700 rpm stirring and left to react for 20 h. Upon experiment completion, the vessel was rapidly cooled in cold water. The reactor was then opened, the reaction mixture recovered by filtration and the compounds present were identified and quantified on a GC-MS (Agilent 6890 with a Zebron ZB-5MS column (Phenomenex) equipped with an Agilent 5973 mass selective detector) and a GC-FID (Agilent 7890 with a Zebron ZB-5 column (Phenomenex) equipped with a flame ionization detector). Pure standard of hydroxy-analogue of valine (Enamine, 95%), glycolaldehyde dimethyl acetal (Sigma Aldrich, 98%) and glycolaldehyde (>99%) was used to quantify the alpha-hydroxy reaction product yield and the amount of unconverted substrate.

Example 3B. Reaction conditions from Example 3A were followed except the molar ratio of acetone/GA was varied. In the solution 1-5 g of acetone was added to 0.1 g of glycolaldehyde and methanol was added to a total solution mass of 10 g. This yielded acetone/GA molar ratios between 10 and 55, showing an optimum/plateau at an acetone/GA molar ratio of between 35 and 55.

TABLE 1

| Experiment | Acetone/GA molar ratio | Yield of valine hydroxy analogue (%) | Yield of MVG (%) |
|---|---|---|---|
| Ex. 3B2B-1 | 1.0 | 9.4 | 20.3 |
| Ex. 3B2B-2 | 5.2 | 25.9 | 12.3 |
| Ex. 3B-3 | 10.3 | 27.6 | 7.5 |
| Ex. 3B-4 | 15.5 | 29.7 | 4.3 |
| Ex. 3B-5 | 20.7 | 30.6 | 4.4 |
| Ex. 3B-6 | 51.7 | 30.6 | 3.0 |

Example 3C. Reaction conditions from Example 3A were followed except the catalyst and substrate loadings were adjusted to 0.1 g catalyst to 20 g acetone (0.4 g GA, L1.6 g acetone, MeOH) and the formation of the valine hydroxy analogue in the presence of Sn--BEA, Ti-BEA and TS-1, respectively, were tested as well as in the absence of catalyst. The tin-containing catalyst Sn-BEA showed by far the highest activity for formation of the desired reaction product under the chosen conditions compared with the titanium-containing catalysts (Ti-BEA and TS-1).

TABLE 2

| Experiment | Catalyst type | Yield of valine hydroxy analogue (%) |
|---|---|---|
| Ex. 3C-1 | No catalyst | 0 |
| Ex. 3C-2 | Sn-BEA | 10.7 |
| Ex. 3C-3 | Ti-BEA | 0.8 |
| Ex. 3C-4 | TS-1 | 1 |

Example 3D. Reactions from Example 3A were followed except water was added to the acetone/GA solution used in the experiment using 0.2 g GA, 0.8 g acetone, 0-1 g water, MeOH was added to a total solution mass of 10 g. It is clear that the <5 wt % water is preferable for the formation of the valine hydroxy analogue.

TABLE 3

| Experiment | Water content (wt %) | Yield of valine hydroxy analogue (%) | Yield of MVG (%) |
|---|---|---|---|
| Ex. 3D-1 | 0 | 29.1 | 14.8 |
| Ex. 3D-2 | 5 | 21.5 | 24.2 |
| Ex. 3D-3 | 10 | 17.3 | 29.4 |

Example 3E. Reaction conditions from Example 3A were followed changing the temperature from 140 ° C. to 180° C. and varying the acetone/GA composition used to 0.2 g GA, 0.8 g acetone, MeOH making up the rest of the 10 g solution used. Here, lower temperatures, preferably <160° C. is desired for the formation of the valine hydroxy analogue.

TABLE 4

| Experiment | Temperature (° C.) | Yield of valine hydroxy analogue(%) | Yield of MVG (%) |
|---|---|---|---|
| Ex. 3E-1 | 140 | 31.6 | 13.3 |
| Ex. 3E-2 | 160 | 29.1 | 14.8 |
| Ex. 3E-3 | 180 | 17.4 | 19.8 |

Example 3F. Reaction conditions from Example 3A were followed varying the amount of Sn-BEA catalyst used in the experiment from 0.1 g to 1 g and changing the acetone/GA solution composition. The reaction mixture was composed of 0.4 g GA, 1.6 g acetone and MeOH making up the rest of the 20 g of solution used in the experiment. Under these reaction conditions, an excess of catalyst is preferable for the production of the valine hydroxy analogue.

TABLE 5

| Experiment | Catalyst amount (g) | Yield of valine hydroxy analogue(%) |
|---|---|---|
| Ex. 3F-1 | 0.1 | 10.7 |
| Ex. 3F-2 | 0.2.5 | 20.8 |
| Ex. 3F-3 | 0.5 | 24.2 |
| Ex. 3F-4 | 1 | 26.7 |

Example 3G. Reaction conditions from Example 3A were followed except the catalyst and substrate loading to 0.5 g catalyst and 10 g acetone solution (0.1 g GA, 2 g acetone, MeOH) testing the formation of the valine hydroxy analogue in the presence of Sn-BEA, Ge-BEA, Hf-BEA and Zn-BEA. The tin-containing catalyst Sn-BEA showed by far the highest activity for formation of the product under the chosen conditions compared with the rest of Lewis acidic catalysts, but importantly, all materials were capable of producing valine hydroxy analogue.

TABLE 6

| Experiment | Catalyst type | Yield of valine hydroxy analogue (%) |
|---|---|---|
| Ex. 3G-1 | Sn-BEA | 32.7 |
| Ex. 3G-2 | Ge- BEA | 1.5 |
| Ex. 3G-3 | Hf- BEA | 6.6 |
| Ex. 3G-4 | Zn- BEA | 3.5 |

Example 4

Preparation of Phenylalanine Hydroxy Analogue from GA and Benzaldehyde

Example 4A. For the preparation of phenylalanine hydroxy analogue, 10 g of a benzaldehyde/GA solution composed of 0.1 g GA, 5 g benzaldehyde and anhydrous methanol was pre-mixed and added to a stainless steel pressure vessel (40 cc, Swagelock) along with 0.50 g of post-synthesized Sn-BEA (Si/Sn=125). This batch reactor was then sealed and placed in a pre-heated oil bath at 160° C. under 700 rpm stirring and left to react for 20 h. Upon experiment completion, the vessels were rapidly cooled in cold water. The reactor was then opened, the reaction mixture recovered by filtration and the products identified and quantified on a GC-MS (Agilent 6890 with a Zebron ZB-5MS column (Phenomenex) equipped with an Agilent 5973 mass selective detector) and a GC-FID (Agilent 7890 with a Zebron ZB-5 column (Phenomenex) equipped with a flame ionization detector). Pure standard of hydroxy-analogue of phenylalanine (ArkPharm, 97%), glycolaldehyde dimethyl acetal (Sigma Aldrich, 98%) and glycolaldehyde (>99%) was used to quantify the product yield and unconverted substrate.

Example 4B. Reaction conditions from Example 4A were followed changing the composition of the benzaldehyde/GA solution. In the solution 1-5 g of benzaldehyde was added to 0.1 g of glycolaldehyde and methanol to a total solution mass of 10 g. This yielded benzaldehyde/GA molar ratios between 5 and 30, showing the highest yield at a benzaldehyde/GA molar ratio of 5.

TABLE 7

| Experiment | Benzaldehyde/GA molar ratio | Yield of phenylalanine hydroxy analogue(%) | Yield of MVG (%) |
|---|---|---|---|
| Ex. 4B-1 | 5.7 | 49.9 | 5.6 |
| Ex. 4B-2 | 8.5 | 34.4 | 0 |
| Ex. 4B-3 | 11.3 | 29.6 | 0 |
| Ex. 4B-4 | 15.6 | 22.0 | 0 |
| Ex. 4B-5 | 28.3 | 7.0 | 0 |

Example 4C. Reaction conditions from Example 4A were followed changing and adding water to the benzaldehyde/GA solution. In the experiments, the benzaldehyde/GA solution was changed to reflect the following composition; 0.2 GA, 0.8 g benzaldehyde, 0-1 g water and MeOH for a total solution mass of 10 g. The highest yield of the phenylalanine hydroxy analogue was found at a water content of 5 wt %.

TABLE 8

| Experiment | Water content (wt %) | Yield of phenylalanine hydroxy analogue(%) | Yield of MVG (%) |
|---|---|---|---|
| Ex. 4C-1 | 0 | 44.1 | 0 |
| Ex. 4C-2 | 5 | 48.3 | 0 |
| Ex. 4C-3 | 10 | 43.9 | 0 |

Example 4D. Reaction conditions from Example 4A were followed changing the temperature from 140° C. to 180° C. The benzaldehyde/GA composition used in this experiment was 0.1 GA, 0.95 g benzaldehyde and MeOH making up the 10 g solution used. Here, higher temperatures preferably >160° C. is desired for the formation of the phenylalanine hydroxy analogue.

TABLE 9

| Experiment | Temperature (° C.) | Yield of phenylalanine hydroxy analogue (%) | Yield of MVG (%) |
|---|---|---|---|
| Ex. 4D-1 | 140 | 39.7 | 5.5 |
| Ex. 4D-2 | 160 | 44.2 | 0 |
| Ex. 4D-3 | 180 | 46.5 | 0 |

Example 5

Preparation of Isoleucine Hydroxy Analogue from GA and Butanone

Example 5A, For the preparation of isoleucine hydroxy analogue, 10 g of a butanone/GA solution composed of 0.1 g GA, 1 g butanone and anhydrous methanol was pre-mixed and added to a stainless steel pressure vessel (40 cc, Swagelock) along with 0.50 g of post-synthesized Sn-BEA (Si/Sn=125), This batch reactor was then sealed and placed in a pre-heated oil bath at 160° C. under 700 rpm stirring and left to react for 20 h. Upon experiment completion, the vessels were rapidly cooled in cold water. The reactor was then opened, the reaction mixture recovered by filtration and the products identified and quantified on a GC-MS (Agilent 6890 with a Zebron ZB-.SMS column (Phenomenex) equipped with an Agilent 5973 mass selective detector) and a GC-FID (Agilent 7890 with a Zebron ZB-5 column (Phenomenex) equipped with a flame ionization detector). Pure standard of hydroxy-analogue of isoleucine (Enamine, 95%), butanone (Sigma Aldrich), glycolaldehyde dimethyl acetal (Sigma Aldrich, 98%) and glycolaldehyde (>99%) was used to quantify the product yield and unconverted substrate, Example 5B. Reaction conditions from Example 5A were followed changing the composition of the butanone/GA solution. In the solution 0.1-3 g of butanone was added to 0.1 g of glycolaldehyde and methanol to a total solution mass of 10 g. This yielded butanone/GA molar ratios between 0.8 and 25, showing the highest yield at a butanone/GA molar ratio of 25.

TABLE 10

| Experiment | Butanone/GA molar ratio | Yield of isoleucine hydroxy analogue(%) | Yield of MVG (%) |
|---|---|---|---|
| Ex. 5B-1 | 0.8 | 6.4 | 30.4 |
| Ex. 5B-2 | 8.3 | 24.2 | 13.4 |
| Ex. 5B-3 | 25 | 49.7 | 8.5 |

Example 5C. Reaction conditions from Example 5A were followed changing the temperature from 140° C. to 180° C. The butanone/GA composition used in this experiment was 0.1 GA, 1 g butanone and MeOH making up the 10 g solution used. As the case for the other ketone in Example 3, lower temperatures preferably <160° C. is desired for the formation of the isoleucine hydroxy analogue.

TABLE 11

| Experiment | Temperature (° C.) | Yield of isoleucine hydroxy analogue (%) | Yield of MVG (%) |
|---|---|---|---|
| Ex. 5C-1 | 140 | 35.3 | 9.1 |
| Ex. 5C-2 | 160 | 24.2 | 13.4 |
| Ex. 5C-3 | 180 | 14.8 | 16.8 |

Example 6

Preparation of Leucine Hydroxy Analogue from GA and Isobutyraldehyde

Example 6A. For the preparation of leucine hydroxy analogue, 10 g of a isobutyraldehyde/GA solution composed of 0.1 g GA, 1. g isobutyraldehyde and anhydrous methanol was pre-mixed and added to a stainless steel pressure vessel (40 cc, Swagelock) along with 0.50 g of post-synthesized Sn-BEA (Si/Sn=125). This batch reactor was then sealed and placed in a pre-heated oil bath at 160° C. under 700 rpm stirring and left to react for 20 h. Upon experiment completion, the vessels were rapidly cooled in cold water. The reactor was then opened, the reaction mixture recovered by filtration and the products identified and quantified on a GC-MS (Agilent 6890 with a Zebron ZB-5MS column (Phenomenex) equipped with an Agilent 5973 mass selective detector) and a GC-FID (Agilent 7890 with a Zebron ZB-5 column (Phenomenex) equipped with a flame ionization detector). Pure standard of hydroxy-analogue of leucine (Enamine, 95%), isobutyraldehyde (To), glycolaldehyde dimethyl acetal (Sigma Aldrich, 98%) and glycolaldehyde (>99%) was used to quantify the product yield and unconverted substrate.

Example 6B. Reaction conditions from Example 6A were followed changing the composition of the isobutyraldehyde/GA solution. In the solution 0.1-3 g of isobutyraldehyde was added to 0.1 g of glycolaldehyde and methanol to a total solution mass of 10 g. This yielded isobutyraldehyde/GA molar ratios between 0.8 and 25, showing the highest yield at an isobutyraldehyde/GA molar ratio of 25.

TABLE 12

| Experiment | isobutyraldehyde/GA molar ratio | Yield of leucine hydroxy analogue(%) | Yield of MVG (%) |
|---|---|---|---|
| Ex. 6B-1 | 0.8 | 11.9 | 14.4 |
| Ex. 6B-2 | 8.3 | 30.5 | 0 |
| Ex. 6B-3 | 25 | 28.1 | 0 |

Example 6C. Reaction conditions from Example 6A were followed changing the temperature from 140° C. to 180° C. The isobutyraldehyde/GA composition used in this experiment was 0.1 GA, 1 g isobutyraldehyde and MeOH making up the 10 g solution used, As the case for the other aldehyde in Example 4, temperature does not have a large influence on the formation of the leucine hydroxy analogue.

TABLE 13

| Experiment | Temperature (° C.) | Yield of leucine hydroxy analogue (%) | Yield of MVG (%) |
|---|---|---|---|
| Ex. 6C-1 | 140 | 28.5 | 2.4 |
| Ex. 6C-2 | 160 | 30.5 | 0 |
| Ex. 6C-3 | 180 | 28.7 | 0 |

The invention claimed is:

1. A process for producing an alpha-hydroxy reaction product of the formula I:

(R)CH(R')—CHOH—COOR"    (I)

wherein
R is —H or —CH₃;
R' is —CH₃, —CH₂CH₃, —CH(CH₃)₂, —C₆H₅, —CH₂SCH₃, —C₈H₆N or —C₃H₃N₂; and
R" is —H, —CH₂CH₃, —CH(CH₃)₂, —CH₂CH₂CH₃, —CH₂CH₂CH₂CH₃, —CH₂CH(CH₃)₂, or —C(CH₃)₃
comprising the steps of:
a) Providing provising a first compound of the formula II:

OHCH₂—CHO    (II)

b) providing a second compound of the formula III:

R—CO—R'    (III)

wherein
R and R' have the meanings as defined above; and
c) reacting the first compound with the second compound in the presence of a Lewis acid catalyst and a reagent R"OH to provide the alpha-hydroxy reaction product, wherein R" has the meaning as defined above, wherein the Lewis acid catalyst comprises one or more active metals selected from the group consisting of Sn, Ti, Pb, Zr, Ge and Hf.

2. The process according to claim 1, wherein R is CH₃.

3. The process according to claim 1, wherein R is H.

4. The process according to claim 1, wherein R" is —H, —CH₃, —CH₂CH₃, or —CH(CH₃)₂.

5. The process according to claim 1, wherein the Lewis acid catalyst has a framework structure, which is selected from the group consisting of BEA, MFI, FAU, MOR, FER, MWW, MCM-41 and SBA-15.

6. The process according to claim 1, wherein the Lewis acid catalyst is Sn-BEA.

7. The process according to claim 1, wherein the Lewis acid catalyst is Sn-MCM-41.

8. The process according to claim 1, wherein the Lewis acid catalyst is a soluble tin salt.

9. The process according to claim 1, wherein in step c), the first and second compounds are reacted at a temperature in the range of from 30 to 220° C.

10. The process according to claim 1, wherein step c) is carried out in a solvent.

11. The process according to claim 10, wherein the solvent is selected from the group consisting of water, methanol, ethanol, propanol, isopropanol, n-butanol, tert-butanol acetone, benzaldehyde, butanone, isobutyraldehyde, 1H-imidazole-4-carbaldehyde, 1H-indole-3-carbaldehyde, methylsulfanyl-acetaldehyde, and mixtures thereof.

12. The process according to claim 1, wherein the R"OH is HOCH₃, wherein in step c) a methyl vinyl glycolate by-product is formed and the molar ratio of alpha-hydroxy reaction product to methyl vinyl glycolate in the range of from 1:1 to 100:1.

13. The process according to claim 1, comprising a subsequent step d) of recovering the alpha hydroxy reaction product.

14. The process according to claim 13 wherein the alpha-hydroxy reaction product is recovered by distillation and/or extraction.

15. The process according to claim 12, further comprising a step d) wherein the alpha hydroxy reaction product is separated from the methyl vinyl glycolate by distillation and/or extraction.

16. The process according to claim 1, wherein R" is H, the process comprising a further step e) of aminating the alpha hydroxy reaction product into the corresponding amino acid.

17. The process according to claim 1, wherein no other aldehydes or ketones are present in step c, other than the first and second compounds.

* * * * *